United States Patent [19]
Jaquet

[11] 3,961,854
[45] June 8, 1976

[54] APPARATUS FOR ORIENTING AND MAINTAINING A ROD IN ANY DIRECTION

[76] Inventor: Henri Jaquet, 9, route des Jeunes, Geneva, Switzerland

[22] Filed: Sept. 10, 1975

[21] Appl. No.: 612,172

[52] U.S. Cl. .................................. 403/59; 403/81; 403/68; 403/188; 403/390; 128/92 A
[51] Int. Cl.² ........................................... F16B 7/06
[58] Field of Search .......... 248/285, 286; 128/84 A, 128/84 B, 84 C, 84 D, 84 R, 92 A; 403/59, 67, 68, 81, 119, 164, 165, 188, 385, 389, 390, 391

[56] References Cited
UNITED STATES PATENTS

| | | | |
|---|---|---|---|
| 2,439,995 | 4/1948 | Thrailkill | 128/92 A X |
| 2,576,527 | 1/1951 | Matthysse | 403/389 X |

FOREIGN PATENTS OR APPLICATIONS

| | | | |
|---|---|---|---|
| 35,674 | 1971 | Japan | 403/391 |
| 125,512 | 4/1919 | United Kingdom | 403/391 |

Primary Examiner—William H. Schultz
Attorney, Agent, or Firm—Haseltine, Lake & Waters

[57] ABSTRACT

Apparatus for orienting and securing a rod in a spatially adjusted position comprising a U-shaped element having opposed parallel branches and a bottom portion connecting the branches. At least two superposed plates are disposed between the branches and the plates have mating faces with grooves therein cooperatively defining a hole receiving a rod. A flange is detachably secured to the branches of the U-shaped element to hold the plates and rod between the branches. The top plate is connected to the flange for rotation about an axis parallel to the branches and the bottom plate is rotatable with respect to the U-shaped element about the same axis. As a consequence, the rod can be angularly rotated with the plates in a plane perpendicular to the branches. A support bar extends longitudinally through the U-shaped element in a direction perpendicular to the above mentioned axis and the plate and rod can be locked in the U-shaped element while the U-shaped element is itself locked on the support bar when the rod is to be immobilized in position.

12 Claims, 8 Drawing Figures

U.S. Patent June 8, 1976 3,961,854
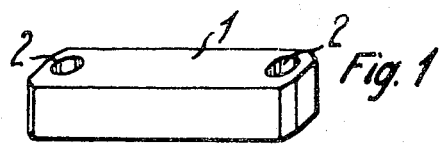
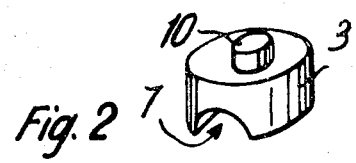
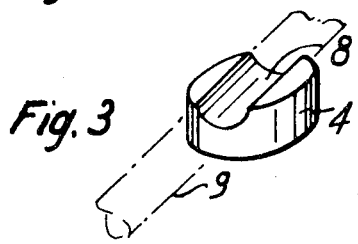
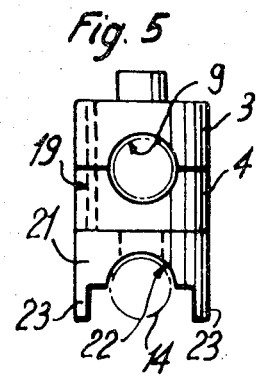
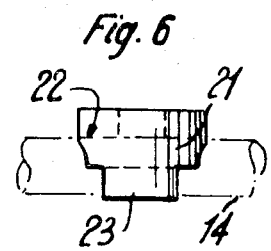
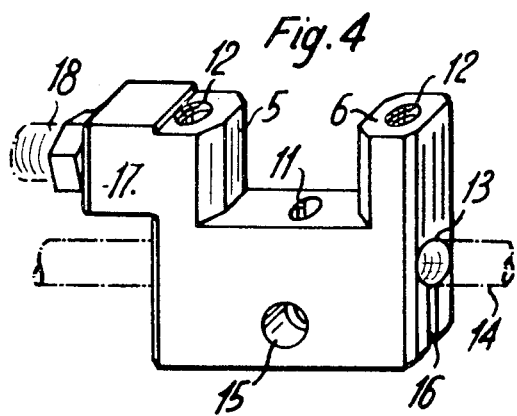
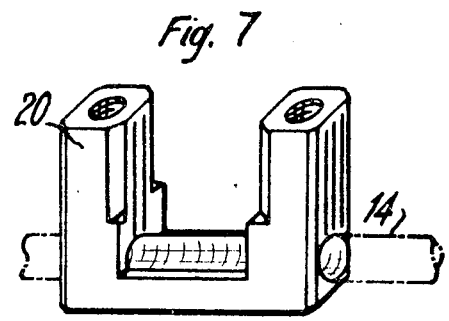
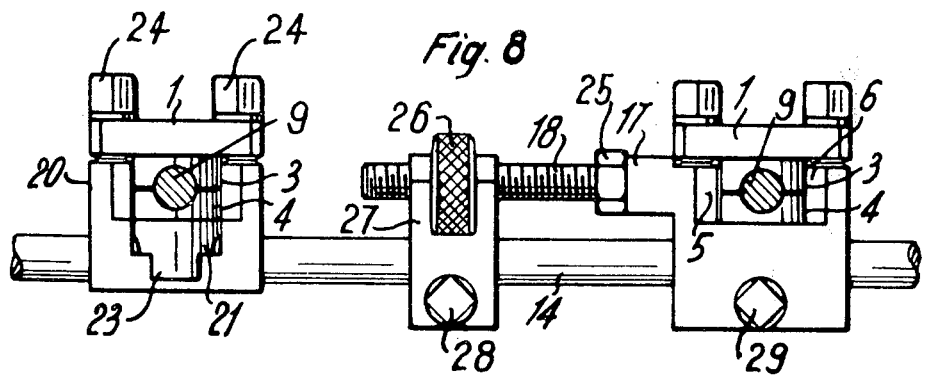

APPARATUS FOR ORIENTING AND MAINTAINING A ROD IN ANY DIRECTION

FIELD OF THE INVENTION

The present invention relates to apparatus for orienting and maintaining a rod or stem in any direction.

BACKGROUND AND SUMMARY OF THE INVENTION

Such apparatus can serve to maintain any object which one desires to place in diverse orientations as, for example, a table lamp, a reflector, etc. and to also employ the same in surgical uses as will be described later.

The present invention is particularly directed to such apparatus.

The apparatus according to the invention comprises a U-shaped element on the branches of which a flange closing the U is detachably secured, at least two cylindrical superposed plates, one of which is rotatably engaged in the flange and the other in the U-shaped element, the adjacent surfaces of the plates each having a diametral groove such that placed face to face these grooves form a hole adapted to receive a rod or stem to be oriented. The rod or stem can be turned with the plates in a plane perpendicular to the branches of the U-shaped element. The U-shaped element has a hole traversing its base in a direction from the foot of one branch to the other and adapted to receive a support bar. The immobilization of the plates with corresponding locking of the rod is obtained by locking of the flange against the extremities of said branches. The immobilization of the U-shaped element on the support bar is obtained either through the intermediary of the above locking by the flange on the U-shaped element or by an independent locking.

The grooves in the plates can be semi-cylindrical or of V-shape or otherwise.

It has been said above that the element according to the invention can be employed in surgical uses. In this case, it will constitute a fixator device for the treatment of bone fractures by the method of pins screwed into the bone.

This method is of itself known and permits by means of the pins and of members joining the same and constituting the fixator device external securing of the said pins and thereby the fractured bone fragments to which they are connected.

The members maintaining these pins are also known in and of themselves permitting their locking as in the manner of a vise and having a stem for coupling to the fixator device.

This comprises for the connection of these members a joinder bar to which the coupling stems are connected by particular elements allowing a displacement of the stems in any orientation desired and their easy immobilization and rigid connection to the joinder bar.

In this case, the joinder bar described above will constitute the support bar of the element cited hereinabove.

It is such application of the invention that the annexed drawing shows two embodiments and a variation given by way of example.

BRIEF DESCRIPTION OF THE DRAWING

FIGS. 1–4 are perspective views of portions of a first embodiment for independent locking of a stem and a joinder bar, FIG. 1 showing a flange, FIGS. 2 and 3 showing plates and FIG. 4 showing a U-shaped element;

FIGS. 5–7 show portions of a second embodiment for simultaneous locking of the stem on the joinder bar; FIG. 5 showing three superposed plates, FIG. 6 showing a side view of the lower plate in FIG. 5 and FIG. 7 showing a U-shaped element which is a simplified version of that of FIG. 4; and FIG. 8 is a side view of an assembled fixator device employing the first and second embodiments of FIGS. 1–4 and 5–7 respectively.

DETAILED DESCRIPTION

Referring to the drawing, FIG. 8 shows an embodiment known as a fixator or ambulatory splint adapted for mechanical application of forces to bone fragments on opposite sides of a fracture. The fixator carries rods or stems 9 which themselves can be transfixion pins or more generally are adapted to support a member carrying such pins, said transfixion pins being intended to pierce the bone fragments for reduction of the fracture and immobilization for healing purposes. It is essential that the rods or stems 9 be properly spaced and angularly oriented in order to provide proper alignment and pressure of the bone fragments. This will be achieved by the construction according to the invention as will be explained hereinafter. However, it is to be understood that the invention is not limited to fixator devices per se but more broadly is directed to means for securing stems in any adjustable spatial relation for whatever purposes desired.

FIG. 8 shows at the left and right thereof, two spaced support assemblies on a joinder bar 14, each support assembly supporting a respective stem 9. Each of these support assemblies will next be described in detail with reference to FIGS. 1–4 and 5–7 respectively.

According to FIGS. 1–4 therein is seen a superposed assembly of a flange 1 with holes 2, cylindrical plates 3 and 4, and a U-shaped element with upstanding branches 5,6. The plates 3,4 are first superposed and inserted between the branches of the U-shaped element whereafter flange 1 is secured to the branches by fasteners extending through holes 2.

Each of the opposed faces of the plates 3,4 has a respective diametral groove 7,8 of a semi-cylindrical shape. When the plates 3,4 are applied against one another these grooves form a hole adapted to receive and surround a stem 9 of a member for support of transfixion pins.

On the surface of each plate opposite the groove, a central boss is formed as seen at 10, the latter being engaged in a recess (not shown) in the flange 1, whereas the boss on the plate 4 (not visible) engages in an opposite recess 11 in the U-shaped element. Thus, the two plates 3,4 superposed and placed between the branches of the U-shaped element can turn around an axis passing through the bosses and extending parallel to the branches 5,6 of the U-shaped element whereas the stem 9 will be oriented as desired in a plane perpendicular to these branches.

By introducing bolts into the holes 2 of the flange 1 and locking them in threaded holes 12 in the branches 5,6 not only can the plates 3,4 be secured in place but by suitably dimensioning the lengths of the branches the assembly of plates and stem can be locked in any position as desired.

The base of the U-shaped element has a hole 13 extending from the face of one of the branches to the face of the other to receive a joinder bar 14.

The assembly of the U-shaped element with the plates and stem will thus be able to turn around bar 14 and it also can be locked by engaging a bolt in threaded holes 15 of ears on opposite sides of a longitudinal slot 16 opening into the hole 13 and extending along the length thereof.

In FIG. 4 the branch 5 of the U-shaped element has a lateral boss 17 supporting an interchangeable threaded stem 18 extending parallel to the hole 13 (and therefore to the bar 14). This structure allows adjustment as will be described in detail later with further reference to FIG. 8.

With regard to the second embodiment of FIGS. 5–7 herein can be found the two plates 3 and 4 identical to those previously described but secured together in rotation by a bolt 19 which is, however, not indispensable. The plates are introduced and maintained between the branches of a U-shaped element 20.

But in the present case the lower plate 4 does not rest on the bottom of the U-shaped element but on a third plate 21 whose lower face also has a diametral groove 22 in the form of a semi-cylinder with two ears 23 at its sides. When the plate 21 is positioned at the bottom of the U-shaped element ears 23 straddle opposite side faces of the U-shaped element. Numeral 24 forming part of this embodiment will be explained later. It can be added at this point that the first embodiment, covered by FIGS. 1 through 4 and the right-hand side of FIG. 8, has parts 1 through 18 and 25 through 29. The second embodiment, just described with reference to FIGS. 5 through 7 and the left-hand third of FIG. 8, includes some of the already described elements, such as 3, 4, 9 and 14, and additionally 19 through 24.

In this position, the groove 22 surrounds the joinder bar 14 and by virtue of a certain play therewith bears on it and the U-shaped element.

Therefore, the plates and the stem 9 and bar 14 can be immobilized in any position by the sole lockage of the flange 1, therefore, without the supplementary bolt in hole 15 in FIG. 4.

In FIG. 8 is shown a fixator device carried on the joinder bar 14 connecting the two assemblies of the elements of FIGS. 1–4 and 5–7. There is only omitted the transfixion pins and their guides solid with the stems 9 which are not part of the invention and are members known in and of themselves.

At the left in FIG. 8 is fixed the assembly according to the second embodiment of FIGS. 5–7. The locking of the flange 1 is effected by means of bolts 24 of square head, but these bolts could be of any other type. It is preferred to utilize only bolts which are locked by means of a wrench, and a screw driver is not preferred in the present case because it is very inconvenient to handle and presents the risk of escape from the screw and injury to the patient.

At the right, with respect to the drawing, the joinder bar 14 carries the assembly according to the second embodiment of FIGS. 1–4. In describing this latter assembly, reference has been previously made to the threaded stem 18 fixed to the boss portion 17 of the U-shaped element. The stem 18 extends parallel to the bar 14 and is immobilized in rotation by a locking screw 25. A knurled nut 26 is threaded on stem 18 and be actuated by hand.

The nut 26 is itself engaged between branches of an element 27 slidable on the bar 14 which can be fixed in place by locking with a locking bolt 28.

By means of this arrangement after having locked the bolt 28 and unlocked a bolt 29 of the U-shaped element, the U-shaped element can be axially adjusted along bar 14 by rotating the knurled nut 26 in one direction or the other. After the desired position has been reached, the bolt 29 is turned to lock the U-shaped element on bar 14.

Thereby in a manner in itself known, a pressure can be exerted on the faces of the fracture by relative movement closer together of the left and right assemblies each of which is connected by fixation pins to one of the bone fragments of the fracture to be reduced.

The facility of locking and the simplicity of adaptation of the represented elements to all positions desired in space allows the fixator device to be capable of uitilization in most cases in practice in which external fixator devices can be used.

What is claimed is:

1. Apparatus for orienting and securing a rod in a spatially adjusted position, comprising a U-shaped element including opposed parallel branches, and a bottom portion connecting said branches, at least two superposed plates having mating faces with grooves therein cooperatively defining a hole, said plates being disposed between said branches a rod engaged in said hole, a flange detachably secured to said branches of said to hold said plates and said rod between said branches, means connecting said plates respectively to said flange and to said bottom portion for rotation about an axis parallel to said branches to enable said rod to be angularly rotated with said plates in a plane perpendicular to said branches, a support bar extending longitudinally through said U-shaped element in a direction perpendicular to said axis, and locking means for locking said plates and said rod in said U-shaped element and for locking said U-shaped element on said support bar.

2. Apparatus as claimed in claim 1, wherein said plates are cylindrical.

3. Apparatus as claimed in claim 1, wherein said locking means includes fasteners detachably locking said flange to said branches and clamping said plates together on said rod.

4. Apparatus as claimed in claim 3, wherein said locking means further includes a transverse fastener extending through said U-shaped element, the latter having two depending ears defined by a longitudinal slot provided in said bottom portion, said transverse fastener passing through said ears beneath said support bar to lock said U-shaped element on said support bar.

5. Apparatus as claimed in claim 4, wherein said fasteners clamp said plates against said bottom portion to lock said rod.

6. Apparatus as claimed in claim 1, wherein said enabling means comprises a lower third superposed plate beneath said at least two plates and rotatably supporting the same.

7. Apparatus as claimed in claim 6, wherein said third plate has a groove therein receiving said support bar.

8. Apparatus as claimed in claim 7, wherein said locking means further includes fasteners detachably locking said flange to said branches and clamping said plates together to immobilize said rod while said lower third plate clampingly bears on said support bar.

9. Apparatus as claimed in claim 8, wherein said third plate includes depending ears straddling said bottom portion of the U-shaped element.

10. Apparatus as claimed in claim 1, further comprising a threaded rod secured to said U-shaped element and extending parallel thereto, a rotatable nut on said threaded rod, a carrier for said nut slidably mounted on said support bar, and means for locking said carrier to said support bar.

11. Apparatus as claimed in claim 1 comprising means connecting said two superposed plates for common rotation.

12. Apparatus as claimed in claim 1, wherein said grooves are of semi-circular shape to define a circular hole.

* * * * *